US009994791B1

(12) United States Patent
Zhang et al.

(10) Patent No.: US 9,994,791 B1
(45) Date of Patent: Jun. 12, 2018

(54) METHOD FOR EXTRACTING LIPIDS FROM ALGAE

(71) Applicants: Chen Zhang, Huntsville, AL (US); James E. Smith, Jr., Huntsville, AL (US)

(72) Inventors: Chen Zhang, Huntsville, AL (US); James E. Smith, Jr., Huntsville, AL (US)

(73) Assignee: Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 0 days. days.

(21) Appl. No.: 14/975,139

(22) Filed: Dec. 18, 2015

(51) Int. Cl.
*C07D 493/00* (2006.01)
*C11B 1/10* (2006.01)

(52) U.S. Cl.
CPC ................ *C11B 1/10* (2013.01); *C11B 1/108* (2013.01)

(58) Field of Classification Search
CPC .......... C11B 1/10; C11B 1/108; C07D 493/00
USPC .......................................................... 549/464
See application file for complete search history.

(56) References Cited

U.S. PATENT DOCUMENTS 5,539,133 A 7/1996 Kohn et al.
8,148,559 B1 4/2012 Walker et al.
8,329,449 B2 12/2012 Poenie et al.
8,772,004 B2 7/2014 Schafron et al.
8,859,270 B2 10/2014 Echevarria Parres
9,085,745 B2 7/2015 Eckelberry et al.
2012/0228224 A1* 9/2012 Kale .......................... C11B 1/10 210/639
2015/0140619 A1* 5/2015 Reddy ...................... C12N 1/12 435/134

FOREIGN PATENT DOCUMENTS

CN 103045352 * 4/2014

OTHER PUBLICATIONS

Coward et al, Harvesting microalgae by CTAB-aided foam flotation increases lipid recovery and improves fatty acid methy ester chracteristics, Biomass and Bioenergy,2014, 67, p. 354-362.*
Park et al, Effects of anionic surfactant on extraction of free fatty acid from Chlorella vulgaris, Bioresource Technology, 2014, 166, p. 620-624.*

* cited by examiner

*Primary Examiner* — Taylor V Oh
(74) *Attorney, Agent, or Firm* — Maynard Cooper & Gate, P.C.; Jon E. Holland

(57) ABSTRACT

Methods for the extraction of intracellular contents from biomass, in particular from algae, are described. The pH level of the algae cell culture is modified and mixed with a surfactant or a combination of surfactants. The algal culture may be subjected to low pressurization using air, inert gas or a gas mixture. Separation of the lipid contents from the treated algae culture is accomplished with an organic solvent or a mixture of organic solvents. The algal debris may be collected at the bottom of the aqueous phase while the biomass is concentrated in the solvent layer.

15 Claims, 2 Drawing Sheets

METHOD FOR EXTRACTING LIPIDS FROM ALGAE

RELATED ART

Biomass is biological material derived from living, or recently living, organisms and has attracted increased attention as a possible alternative fuel source. In particular, lipid compounds from biomass can be processed to generate biofuels as a source of renewable energy. Algae have the natural ability to grow rapidly and accumulate large amounts of such lipids within their cells and, as such, may be used as a biomass for use as an alternative fuel source.

The successful extraction of algae-based lipids depends on the selection of the appropriate algal strains and the selection of the most economically viable lipid extraction method. Extracting lipids, however, is one of the most difficult, but important, steps in biofuel production based on large scale algae harvesting. Algae have a tough cell wall that must be disrupted to effectively obtain the useful intracellular contents. Conventional algae lipid extraction generally involves dewatering, also known as dewetting, before the extraction process, because residual water in wet algal biomass hinders mass transfer of the lipids from the cell, leading to a decrease in the efficiency of lipid extraction.

Dewatering, however, requires energy input to dehydrate the algae culture to dryness, thereby making the lipid contents more available for extraction by organic solvents. The dehydration process is highly energy intensive and the energy input usually exceeds the recovered fuel energy values. In addition, many of the organic solvents used in the conventional methods are regarded as highly-toxic.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure generally pertains to methods for the extraction of intracellular contents from biomass, in particular from algae, in aqueous suspension, and for harvesting the algal debris. In one embodiment, the pH level of the algae cell culture is modified and mixed with a surfactant or a combination of surfactants. In an additional embodiment, the algal culture may be subjected to low pressurization using air, inert gas or a gas mixture. Separation of the lipid contents from the treated algae culture is accomplished with an organic solvent or a mixture of organic solvents. The algal debris may be collected at the bottom of the aqueous phase while the biomass is concentrated in the solvent layer.

As used herein, the term "about" means plus or minus approximately ten percent of a numerical value, such that "about 20° C." indicates a temperature between approximately 18° C. and 22° C.

As used herein, the term "algae" includes, but is not limited to, microalgae. Some non-limiting examples of algae include *Nannochloropsis salina, Dunaliella salina*, and other algae suitable for lipid extraction known in the art.

Lipids are a group of naturally occurring molecules that include fats, waxes, sterols, fat-soluble vitamins (such as vitamins A, D, E, and K), monoglycerides, diglycerides, triglycerides, phospholipids, and others. Most lipids are soluble in organic solvents, for instance non-polar solvents, but insoluble in water. In one embodiment, lipids from algae may be used in the methods of the present disclosure. In an additional embodiment, the methods of the present disclosure may be used to isolate lipids from non-algae sources, for example, plant oils, animal oils and synthetic oils.

Figure 1:
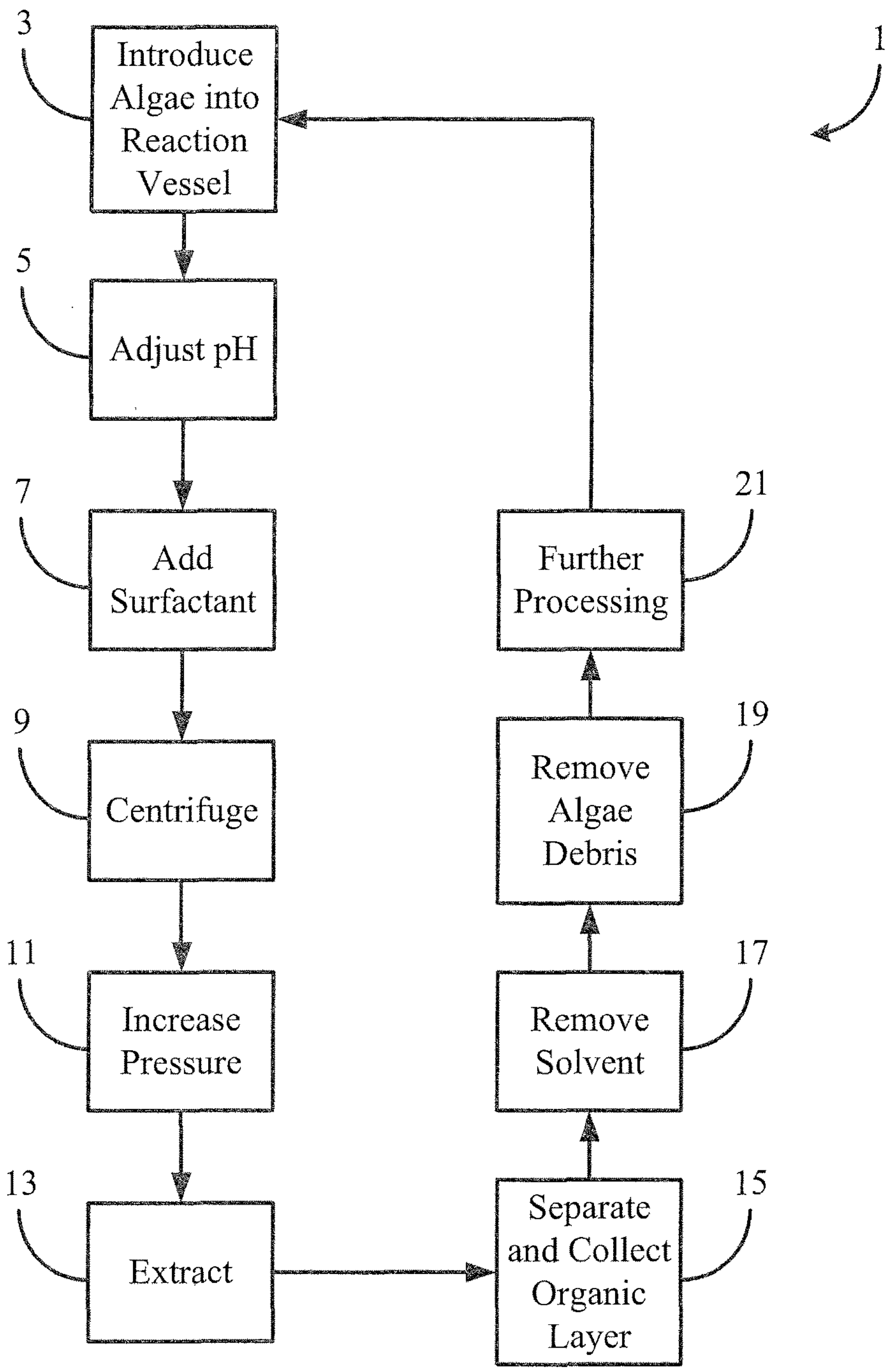
FIG. 1 is a flow chart of an exemplary method for extracting lipids from algae.

FIG. 1 depicts an exemplary flow chart of a method 1 of extracting intracellular lipid contents from a biomass, in particular algal cells. In one embodiment, the extraction process 1 is performed at temperatures between 0° C. to 100° C. In an additional embodiment, the extraction process 1 is performed at room temperature, i.e., between about 20° C. to 26° C. The extraction process 1 may be performed at other temperature ranges in other embodiments.

Referring again to FIG. 1, as indicated by box 3, an aqueous algae culture is obtained from any source commonly known in the art. The algal culture containing algal cells can be concentrated or diluted, but typically is used as grown in the environment, i.e., without isolation of the algae cells. In this embodiment of the disclosure, it is not necessary to dry or dewet the algae culture. This is an advantage of the present disclosure compared to conventional algae lipid extraction, which includes a dewetting process that requires significant energy input and is highly energy intensive. Eliminating the dewetting step, as disclosed herein, reduces the costs of the presently described extraction method 1. Nonetheless, in certain embodiments, the algae cell mass is dried, for example by freeze-drying, spray-drying and heat-drying, sun-drying, or other drying method known in the art, prior to the extraction process. Further, in certain embodiments, the algae culture may contain a mixture of, i.e., more than one, algae strains.

Referring again to FIG. 1, the pH level of the liquid algal culture is then modified to optimize lipid extraction, as indicated in box 5. The pH level may be increased or decreased from the pH present in a typical algal growing environment. The optimal pH level for lipid extraction is dependent upon the strain of the algae in use. The pH modifying agent may comprise a chemical, a combination of chemicals, a gas, or a combination of gases. Such pH modifying agents include, but are not limited to, citric acid, hydrobromic acid, hydrochloric acid, hydroiodic acid, nitric acid, perchloric acid, phosphoric acid, and sulfuric acid. In one embodiment, the pH level of the culture is lowered by the addition of an acid, for instance citric acid. In this embodiment, the lower pH weakens the algae cell walls by affecting the tertiary structure of the proteins (intrinsic and extrinsic) held within the bi-layer of the phospholipid membrane, allowing extraction of the algal intracellular contents. In one example, lowering the acidity of *Nannochloropsis salina* culture from its natural level of pH 7 to about pH 6 causes disruption of the algae cell walls sufficient for lipid extraction by the currently described method 1. Modification of the pH results in the production of an algae solution.

As indicated by box 7, the algal culture is next mixed with a surfactant or a combination of surfactants to further assist in releasing the intercellular contents. Although the extraction method 1 described in FIG. 1 illustrates adding the surfactant 7 after adjusting the pH (box 5), the mixing of the algal culture with a surfactant or a combination of surfactants may be accomplished prior to, during or after pH modification. Surfactants are compounds that lower the surface tension between two liquids, or a liquid and a solid. Generally, surfactants are amphiphilic organic compounds containing both hydrophobic group tails and hydrophilic group heads. A surfactant contains both a water-insoluble (or oil soluble) component and a water-soluble component.

One common class of surfactants is the detergents. In solution, detergents dissociate aggregates and unfold proteins and are therefore key reagents in the extraction of proteins from cells via lysis of the cells and tissues. Detergents act by disorganizing the cell membrane lipid bilayer (e.g., sodium dodecyl sulfate (SDS), Triton X-100, X-114, CHAPS, DOC, and NP-40), and by solubilizing proteins. Milder detergents such as octyl thioglucoside, octyl glucoside or dodecyl maltoside are used to solubilize membrane proteins such as enzymes and receptors without denaturing them. Proteins are often treated with a detergent, for instance SDS, to cause denaturation of the native tertiary and quaternary structures. The proteins may then be separated the according to their molecular weight.

In one embodiment, the one or more surfactants are preferably chosen from anionic surfactants, non-ionic surfactants or mixtures thereof. In an additional embodiment, sodium dodecylbenzenesulfonate is utilized in treating the algal cells (box 40), but other anionic surfactants are possible in other embodiments including, but not limited to sodium dodecyl sulfate, sodium lauryl ether sulfate, sodium lauryl sulfate and ammonium lauryl sulfate. Non-ionic surfactants include, but are not limited to, cetyl alcohol, stearyl alcohol, cocamide monoethanolamine (MEA) and cocamide diethanolamine (DEA). The surfactant concentration may vary based upon on the concentration of algal cells in the reaction mixture. In one embodiment, the concentration may be between 0% and 90% (w/w) in water. In an additional embodiment, an algae culture containing 3 grams of algae cells per liter of water requires an approximate 1 percent solution of sodium dodecylbenzenesulfonate (w/w). The non-solubilized material may then be harvested by centrifugation or other means (box 9) and discarded.

In an additional embodiment indicated by box 11, the mixture of pH-modified algal culture and surfactants may be subject to pressurization using gas or a gas mixture. In one exemplary embodiment, a 100% carbon dioxide gas or mixture of carbon dioxide and an additional gas may be used to provide the applicable pressure to the algal culture. Additionally, the algal culture may be pressurized in a pressure reactor or a conduit. The pressurization procedure may occur as a batch or a continuous reaction. The pressure applied to the culture may range, for example, from about standard atmospheric pressure to about 5000 psig. In one embodiment, the culture is pressurized to about 100 psig. The duration of the pressurization may range from instantaneous (i.e., 0 seconds) to 48 hours. In one embodiment, the culture is pressurized for less than one minute (e.g., a *Nannochioropsis salina* culture). The pressurization step may be accomplished after the pH modification step (box 5) and surfactant treatment step (box 7).

Bio-lipids, for example lipids isolated from algae, are generally soluble in organic solvents but insoluble in water. As a result, the lipid matter of the algal cell may still be contained within the disrupted cell wall after acid treatment (box 5) and surfactant treatment (box 7) as it is surrounded by water within the aqueous culture. The algal lipids present in the aqueous reaction mixture are not soluble in water and are difficult to extract from the algae cells. In addition, surfactants contain both a water soluble hydrophilic group, and water soluble (or oil soluble) hydrophobic group. As a result, a surfactant will diffuse in both water and oil. This water insoluble hydrophobic group extends out the of the bulk aqueous phase while aqueous soluble hydrophilic group remains in the aqueous phase.

Referring again to FIG. 1, an extraction process is used to further isolate the algal lipids from the treated aqueous sample (box 13). This process may be described as a liquid-liquid extraction. In such a liquid-liquid extraction, the solute of interest partitions between two immiscible phases. Generally, one phase is aqueous and the other phase is an organic solvent. Because the phases are immiscible they form two layers, with the denser phase on the bottom. The solute is initially present in one of the two phases as the immiscible nature of the two solvents acts to separate and select the compounds to be isolated. The process of extraction uses the solubility differences of the different substances in the solution to selectively draw the desired product into one of the layers. Extraction methods differ depending upon the density of the solvent being used. Extraction efficiency, i.e., the percentage of solute moving from one phase to the other, is determined by the equilibrium constant for the solute's partitioning between the phases and any other reactions involving the solute. Here, the desired compounds, for example algal lipids, are pulled from a first phase into a second phase where the phases are not miscible. The extraction process results in the production of an extraction solution.

Many extraction systems include water as one of the solvents because water is highly polar and immiscible with most organic solvents. In an additional embodiment, ethyl acetate, an organic compound with the formula $C_4H_8O_2$, is used as a solvent during algal biomass extraction. Ethyl acetate is the ester of ethanol and acetic acid and is fairly volatile at room temperature, having a boiling point of 77° C. Due to these properties, it can be removed from a sample by heating, for example in a hot water bath, and providing ventilation with compressed air. Other advantages of ethyl acetate includes its low cost, its ability to rapidly decompose, and its low toxicity.

Referring again to FIG. 1, the treated aqueous sample (box 11) is mixed with the organic solvent utilized in the solvent extraction process (box 13), for example ethyl acetate. After mixing, the aqueous and organic layers are separated, as indicated by box 15. Thorough mixing is desirable as the two solutions should be in contact with each other to allow the algal lipids to be extracted into a single layer.

Figure 2:
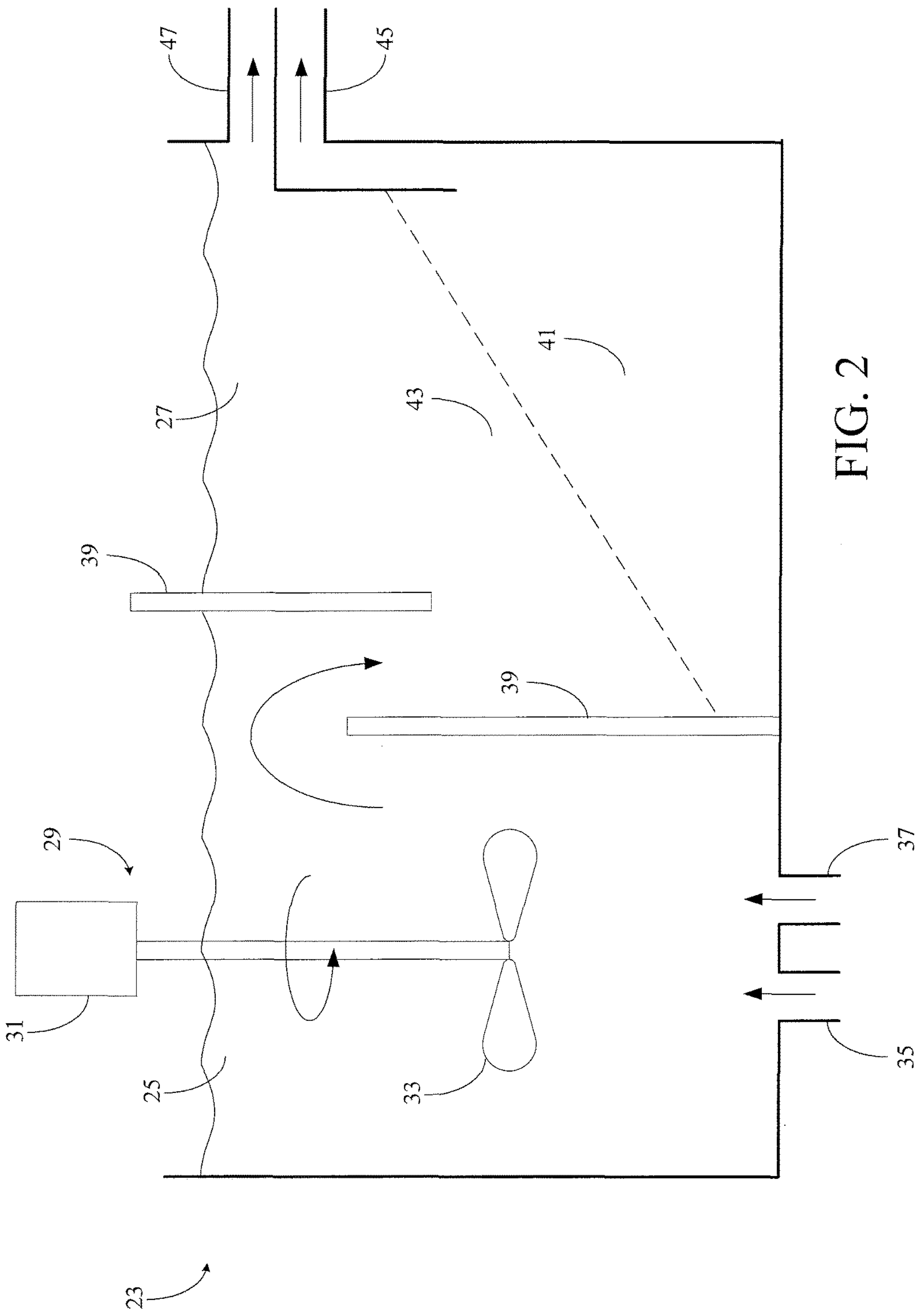
FIG. 2 is an illustration of an exemplary mixer/settler.

In an additional embodiment, the extraction process 1 may be performed in a conventional laboratory setting, for instance using a separation funnel. In an additional embodiment, larger scale isolation of algal lipids may involve extraction using a mixer/settler system 23. Mixer settlers 23 are a type of equipment used in the solvent extraction process. One type of mixer/settler 23 is illustrated in FIG. 2. This exemplary mixer/settler 23 comprises a first stage or mixing chamber 25 that mixes the phases together followed by a settling stage or chamber 27 that allows the phases to separate by gravity.

The mixing chamber 25 comprises an agitator 29 which contacts the aqueous and organic solutions to carry out the transfer of solute(s). The agitator 29 is equipped with a motor 31 which drives a mixing apparatus 33 for agitating the solutions in the mixing chamber. In the embodiment illustrated in FIG. 2, the mixer 23 includes a heavy phase inlet 35 and a light phase inlet 37. The apparatus 33 mixes the two solutions, and transfers this emulsion to the associated settler 27. In one embodiment, for example in large-scale industrial applications, the mixer 23 may comprise more than one stage (not shown in FIG. 2). Use of multiple stages increases the reaction time.

In one embodiment the settling chamber 27 separates the two phases separate by static decantation. In addition, coalescence plates 39 may be utilized to facilitate the separation of the emulsion into two phases (heavy 41 and light 43). The two phases 41 and 43 are then removed separately from the mixer/settler 23 through two outlets 45 and 47.

In one embodiment, a balance of non-polar solvent capable of dissolving neutral lipids and polar solvents capable of extracting complex lipids can be used to optimize extraction. In this embodiment, at least one of the solvents is at least somewhat soluble in water. Although the extraction process 13 is indicated in FIG. 1 as occurring after the pressurization process 11, extraction may also occur before pressurization.

Referring again to FIG. 1, the organic layer containing the algal lipids is then collected for further processing, as illustrated in box 15. Next, the solvent, (e.g., ethyl acetate) is then removed from the organic layer (box 17). In the embodiment where the solvent comprises ethyl acetate, the removal process 17 may be accomplished, for instance, through evaporation. Next, the algal debris may then be collected and removed from the sample, for instance by centrifugation (box 19). As illustrated in box 21, the organic layer containing the algal lipids may then undergo further processing steps, for instance a transesterification process. In yet another embodiment, the solvent removal process 17 may be eliminated from the current method and the organic layer containing the isolated algal lipids may then be directly processed at steps 19 and 21. In one embodiment, the extraction method 1 may be repeated a plurality of times to improve yield. A typical algal lipid yield after one cycle of the extraction method 1 is approximately 90%-98% of the total lipid content for the algae *Nannochioropsis salina.*

In one embodiment, the size of the one or more surfactants used at step 7 is large enough so that they remain in the aqueous phase and not in the organic layer. This is particularly important when utilizing ethyl acetate as the solvent. In addition, the organic solvent may have slight solubility in water. In one embodiment, the organic solvent has a solubility of about 4-6% in aqueous solutions. Solubility less than about 4-6% may not be sufficient to pull the algal lipids from the aqueous layer. In addition, the surfactant should form a strong hydrophilic bond with water so as to overcome the lipophilic bond strength between the lipids and the organic solvent. This allows the algal debris to remain in the aqueous while the lipids are drawn to the organic phase.

Any remaining aqueous solution may be discarded as it has low concentration of sodium dodecylbenzenesulfonate and ethyl acetate which are both easily biodegradable. In an alternate embodiment, the remaining aqueous solution may be treated to recycle sodium dodecylbenzenesulfonate and ethyl acetate.

Although the figures herein may show a specific order of method steps, the order of the steps may differ from what is depicted. Also, two or more steps may be performed concurrently or with partial concurrence. All such variations are within the scope of the application.

It should be understood that the identified embodiments are offered by way of example only. Other substitutions, modifications, changes and omissions may be made in the design, operating conditions and arrangement of the embodiments without departing from the scope of the present application. Accordingly, the present application is not limited to a particular embodiment, but extends to various modifications that nevertheless fall within the scope of the application. It should also be understood that the phraseology and terminology employed herein is for the purpose of description only and should not be regarded as limiting.

Now, therefore, the following is claimed:

1. A method for extracting lipids from algae, comprising:

introducing an aqueous algae culture into a reaction vessel;

adjusting the pH of the algae culture, thus creating an algae solution;

adding a surfactant to algae solution, wherein the surfactant comprises at least one anionic surfactant;

extracting the solution with a partially water soluble organic solvent, thus creating an extraction solution, wherein the partially water soluble organic solvent comprises ethyl acetate; and isolating the algae lipids from the organic layer of the extraction solution.

2. The method of claim 1, further comprising adjusting the pressure of the solution after adding the surfactant.

3. The method of claim 2, where the pressure is adjusted to approximately 100 psig.

4. The method of claim 2, wherein the pressure is adjusted using air.

5. The method of claim 2, wherein the pressure is adjusted using a gas.

6. The method of claim 5, wherein the gas is carbon dioxide.

7. The method of claim 1, further comprising removing the solvent from the extraction solution.

8. The method of claim 1, wherein the organic solvent has an approximate solubility of about 0.000001% to 80% in water.

9. The method of claim 1, further comprising centrifuging the algae solution to remove algae cell debris.

10. The method of claim 1, where the extraction is performed in a mixer/settler.

11. The method of claim 1, wherein the method is carried out at room temperature.

12. The method of claim 1, wherein the algae culture comprises *Nannochloropsis salina.*

13. The method of claim 1, wherein the surfactant is a detergent.

14. The method of claim 1, wherein the surfactant is used at a concentration of 1% w/vol.

15. The method of claim 8, wherein the organic solvent has a solubility of about 4-6% in water.

* * * * *